United States Patent [19]

Kasafirek et al.

[11] Patent Number: 4,554,100
[45] Date of Patent: Nov. 19, 1985

[54] ALKYLAMIDES OF CARBOXYALKANOYL PEPTIDES AND METHOD FOR PREPARATION THEREOF

[75] Inventors: Evzen Kasafirek; Premysl Fric; Jan Slaby; Alena Roubalova, all of Prague, Czechoslovakia

[73] Assignee: Spofa, Spojene podniky pro zdravotnickou vyrobu, Prague, Czechoslovakia

[21] Appl. No.: 406,168

[22] Filed: Aug. 9, 1982

[30] Foreign Application Priority Data

Aug. 7, 1981 [CS] Czechoslovakia ............... 5977-81

[51] Int. Cl.$^4$ ........................................... C07C 103/52
[52] U.S. Cl. ............................................ 260/112.5 R
[58] Field of Search ................. 424/177; 260/112.5 R

[56] References Cited

U.S. PATENT DOCUMENTS 4,187,216 2/1980 Hassall et al. ............... 260/112.5 R

FOREIGN PATENT DOCUMENTS 0026243 6/1977 Australia .

OTHER PUBLICATIONS

*Chemical Abstracts*, 96, 1982, p. 237, Abstract No. 48067m, Kleine et al.

Hochstrasser et al., *Hoppe-Seyler's Z. Physiol. Chem.*, 362, 1369–1375, (1981).

Bayer, *Biochemical and Biophysical Research Communications*, 32, No. 5, 739–902, (1968).

K. Blaha, P. Malon, *Peptides*, Walter de Gruyter & Co., Berlin, 1982, pp. 639–642.

Kasafirek et al., *Experientia*, vol. 39, 1983, pp. 374–375.

Kasafirek, *FEBS Letters*, vol. 40, No. 2, 1974, pp. 353–356.

Kasafirek et al., *Eur. J. Biochem.*, vol. 89, 1976, pp. 1–13.

*Primary Examiner*—Delbert R. Phillips
*Assistant Examiner*—F. T. Moezie

[57] ABSTRACT

A method is described for the preparation of novel alkylamides of carboxyalkanoyl peptides of the formula

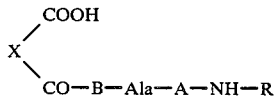

wherein R is an aralky or an alkyl group of 1–5 carbon atoms, A is a residue of peptidically bound proline or alanine, B is a straight bond or a residue of peptidically bound proline or alanine and X is a CH=CH group or a methylene group of 1–3 carbon atoms.

The described compounds are capable of inhibiting elastase.

2 Claims, No Drawings

ALKYLAMIDES OF CARBOXYALKANOYL PEPTIDES AND METHOD FOR PREPARATION THEREOF

This invention relates to a process for the preparation of alkylamides of carboxyalkanoyl peptides and to the peptides so produced.

The alkylamides of dipeptides are known to be effective inhibitors of elastase (see Belgian Pat. Nos. 855,851 and 856,064). Additionally, the dipeptides evidence characteristics which are akin to amino acid composition optimums for elastolytic substances, for example alanyl-alanine or alanyl-proline. Previous studies concerning the optimization of a substrate for pancreatic elastase revealed the presence of an electrostatic bond between $P_4$-$S_4$ and $P_5$-$S_5$ (see I. Schechter et al, Biochem. Biophys. Res. Commun. 32, 898 (1968) was of great significance with regard to the interaction between substrate and enzyme, the bond being viewed as related to a primary interaction (see Eur. J. Biochem. 69, 1 (1976), FEBS Lett. 40, 353 (1974).

The earlier work also led to the surprising discovery that the carboxy group in the N-terminal part of the inhibitor as compared with the hydrophobic residue, such as an acetyl, substantially enhances inhibition capacity in the same manner as it enhances the constants of elastolytic hydrolysis of substrates of this type. It is further known that the properties of an elastolytic inhibitor are dependent upon the length of the peptide chain as well as at the substrate (eur. J. Biochem. 69, 1, 1976), higher inhibition capacity being present with a tripeptide than with a dipeptide. Experiments with vitro inhibition constants (Ki) for the alkylamides of 3-carboxypropionyl and 4-carboxybutyryl di and tripeptides were determined using pancreatic elastase and chromogenic substrates of p-nitroanilides of succinyl or glutaryl tetraalanines, the results of which are set forth in Table 1, below. Inhibition constant of the inhibitors described herein were also determined using human elastase, that is, human duodenal elastase after stimulation with cholecystokinine ($E_1$) or lyophilized human pancreated fluid obtained by cannulation of the pancreatic duct outlet ($E_2$), and they were then compared with swine's pancreatic elastase ($E_3$), the results of which are set forth in Table 2, below.

TABLE 1

Inhibition constants (Ki) of alkylamides of acylated di- and tripeptides.

| Inhibitor | Ki (μmol) | |
|---|---|---|
| | Suc—(Ala)$_4$—NAn | Glt—(Ala)$_4$—NAn |
| Suc—(ala)$_2$—NH—Et | 95.2 | 166 |
| Glt—(Ala)$_2$—NH—Et | 68.1 | 109 |
| Suc—(Ala)$_2$—NH—EtPh | 1456 | 666 |
| Glt—(Ala)$_2$—NH—EtPh | 982 | 770 |
| Suc—(Ala)$_3$—NH—Me | 510 | 680 |
| Glt—(Ala)$_3$—NH—Me | 280 | 320 |
| Suc—(Ala)$_3$—NH—Et | 20 | 29 |
| Glt—(Ala)—$_3$—NH—Et | 8.8 | 8.4 |
| Mal—(Ala)$_3$—NH—Et | 35 | 30 |
| Ac—(Ala)$_3$—NH—Et | 28 | 46 |
| Suc—(Ala)$_3$—NH—Pr | 6.8 | 4.5 |
| Glt—(Ala)$_3$—NH—Pr | 2.5 | 2.5 |
| Suc—(Ala)$_3$—NH—iBu | 816 | 1474 |
| Glt—(Ala)$_3$—NH—iBu | 668 | 794 |
| Suc—Ala—Pro—NH—Et | 111 | 80 |
| Suc—Ala—Pro—NH—iBu | 2042 | 5747 |
| Suc—Ala—Ala—Pro—NH—Et | 2.5 | 4.7 |
| Glt—Ala—Ala—Pro—NH—Et | 1.6 | 2.7 |

TABLE 2

Inhibition constants (Ki) of alkylamides of acylated tripeptides.

| | Ki (μmol) | | | | | |
|---|---|---|---|---|---|---|
| | Suc—(Ala)$_4$—NAn | | | Glt—(Ala)$_4$—NAn | | |
| | $E_1$ | $E_2$ | $E_3$ | $E_1$ | $E_2$ | $E_3$ |
| Ac—(Ala)$_3$—NH—Et | 238 | 69 | 28 | 123 | 117 | 46 |
| Mal—(Ala)$_3$—NH—Et | 87 | 69 | 35 | 73 | 117 | 30 |
| Suc—(Ala)$_3$—NH—Et | 76 | 29 | 20 | 89 | 47 | 29 |
| Glt—(Ala)$_3$—NH—Et | 15 | 7.4 | 8.8 | 19 | 19 | 8.4 |
| Suc—Ala—Ala—Pro—NH—Et | 14 | 23 | 2.5 | 19 | 17 | 4.7 |
| Glt—Ala—Ala—Pro—NH—Et | 10 | 2.9 | 1.6 | 12 | 13.8 | 2.7 |
| Suc—(Ala)$_3$—NH—Pr | 12 | 13 | 6.8 | 21 | 14 | 4.5 |
| Glt—(Ala)$_3$—NH—Pr | 11 | 3.8 | 2.5 | 7.2 | 4.5 | 2.5 |

Suc = succinyl;
Glt = glutaryl;
NAn = nitroanilide;
Et = ethyl,
Pr = propyl;
Mal = 3-carboxyacryolyl i.e. maleyl.

In vivo experimentation with experimental pancreatitis in rats, induced by the nitroorgan application of sodium desoxycholate revealed that lower level of serum amylase with the simultaneous application of 20 mg intraperitoneally of Glt-(Ala)$_3$-NH-Et, Glt-Ala-Ala-Pro-NH-Et and especially Glt-Ala-Ala-Pro-Nh-Pr in a dose of 20 mg per rat was found to suppress the development of oedema induced by subcutaneous injection of elastase in the rats paws by 20 to 40%.

When compared with known alkanoyl derivatives (dipeptides), See Biochem. Chem. 8, 299 (1979) a significant enhancement in the inhibition of elastolytic hydrolysis is evidenced, so suggesting the significance of the character of N-terminal substituents.

The alkylamides of carboxyalkanoyl peptides described herein are of the formula

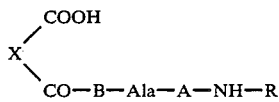

wherein

R is a straight or branched chain alkyl group of 1–5 carbon atoms or an aralkyl group, A is a residue of peptidically bound proline or alanine, B is a residue of peptidically bound proline or alanine or excluded, X is selected from the group consisting of $(CH_2)_n$ and $CH=CH$ groups, n being an integer from 1–3.

The described peptides are obtained by reacting a compound of the formula $$A-NH-R \qquad (2)$$

wherein R and A are as described above with a compound of the formula $$X-B-Ala \qquad (3)$$

wherein B is as defined above and Y is a readily removed protecting group such as a benzyloxycarbonyl group. Following removal of the protecting group the resultant intermediate is reacted with a reactive derivative of dicarboxylic acid of the formula

 (4)

wherein X is as defined above with its anhydride, hemihalogenide, hemi-ester or hemi-amide.

The synthesis of these biologically active peptides is effected, from a mechanical standpoint, by fragment condensation in solution, by stepwise aminoacidic building or by synthesis with a solid carrier.

Protecting groups employed in the practice of the present invention may be selected from among urethanes (benzyloxycarbonyl), groups which are unstable in weakly acidic media such as tert-butyloxycarbonyl or o-nitrobenzene sulphenyl, or groups capable of being reduced with metals or electrolytically, such as 2 halogene-ethyloxycarbonyl.

Condensation reactions may be effected by the azide method, the carbondiimide method and the method of mixed anhydrides or other methods employed for preparing peptides.

Several examples of the practice of the present invention are set forth below. These examples are merely for purposes of exposition and are not to be construed as limiting.

EXAMPLE 1

Benzyloxycarbonyl Alanine Ethylamide 14 ml. of N-ethyl piperidine was added to a solution of 23.3 grams of benzyloxycarbonyl alanine in 100 ml. of tetrahydrofuran and, after cooling to −10 degrees C., 14 ml. of sec. butyl chlorformate was added. Next, the mixture was stirred for 8 minutes and cooled to −6 degrees C. Then 30 ml. of a 4.1 solution of ethylamine in tetrahydrofuran was added. After 30 minutes of stirring at 0 degrees C. and 2 hours of stirring at room temperature, the reaction solution was evaporated, gradually shaken with a 5% solution of sodium hydrogen carbonate, with water, dried with anhydrous sodium carbonate, and evaporated. The evaporation residue was crystallized from ethyl acetate (30 ml.) and petroleum ether. 18.1 g of a product having a melting point of 116 to 117 degrees C. was obtained.

Alanine Ethylamide Hydrobromide 10 grams of benzyloxycarbonyl alanine ethylamide was treated with 40 ml. of 36% hydrogen bromide in glacial acetic acid. Then, 150 ml. of ether was poured over the mixture and, after 1 hour, a crystalline product separated. The product was filtered off, thoroughly washed with ether and dried in a desiccator over phosphorus pentoxide and sodium hydroxide. 7.7 g of the hydrobromide, having a melting point of 224 to 226 degrees C., was obtained.

$R_f$ 0.26/$S_1$, 0.58$S_2$.

$S_1$: n-butyl alcohol—acetic acid—water (4:1:1).

$S_2$: n-butyl alcohol—acetic acid—pyridine—water (15:3:10:6).

Benzyloxycarbonylalanyl-alanyl Alanine Ethylamide

To a solution of 3.08 grams of benzyloxycarbonylalanyl alanine hydrazide in 100 ml. of tetrahydrofuran there was added 4 ml. of an azeotropic hydrochloric acid solution comprising 690 mg. of sodium nitrate in 2.8 ml. of water, the addition being effected at a temperature of −12 degrees C. After 8 minutes of stirring and cooling to −10 degrees C., the reaction solution was diluted with 200 ml. of pre-cooled ethyl acetate. Then, an organic phase was extracted with a solution of sodium hydrogen carbonate in brine (3%) at −15 degrees C., dried with sodium sulfate and added to a pre-cooled solution (−10 degrees C.) of alanine ethylamide in 40 ml. of dimethylformamide prepared from 1.97 grams of N-ethylpiperidine. After 12 hours at a temperature of 0 degrees C., the solution was evaporated and the solid evaporation residue crystallized from a mixture of 50 ml. of 2-propyl alcohol and 50 ml. of dimethylformamide by the addition of 250 ml. of water. 2.71 g of a product having a melting point of 271 to 273 degrees C. was obtained.

$[\alpha]_D^{20} -8.3°$ (c 0.3; dimethylformamide).

For $C_{19}H_{28}N_4O_5$ (392.5): calculated: 58.15% C, 7.19% H, 14.28% N; found: 57.97% C, 7.27% H, 13.93% N.

Alanyl-alanyl Alanine Ethylamide 1 gram of Benzyloxycarbonylalanyl-alanyl-alanine ethylamide was treated with 3 ml. of 36% hydrogen bromide in acetic acid and after 1 hour, the original solution was treated with 30 ml. of ether. Separated hydrobromide was filtered off, dried for two hours in a desiccator over phosphorus pentoxide and sodium hydroxide, and then dissolved in 20 ml. of 90% aqueous methyl alcohol and deionized at Zerolit FF in OH-cyclus in methyl alcohol. Methanolic eluate was then evaporated and the evaporation residue dried by azeotropic distillation from a mixture of methyl alcohol and benzene. The evaporation residue was crystallized from 10 ml. of methyl alcohol (10 ml.) and 30 ml. of ether. 495 mg of a product having a melting point of 259 to 260 degrees C. was obtained.

$[\alpha]_D^{20} -67.1°$ (c 0.3; methyl alcohol).

$R_f 0.14/S_1$; $0.58/S_2$.

For $C_{11}H_{22}N_4O_3$ (258.3): calculated: 51.15% C, 8.58% H, 21.69% N; found: 50.82% C, 8.63% H, 21.37% N.

An analytical sample of alanyl-alanyl alanine ethylamide hydrobromide was crystallized from methyl alcohol and ether; melting point 284 to 289 degrees C.

For $C_{11}H_{22}N_4O_6 \cdot HBr$ (339.2): calculated: 38.95% C, 6.83% H, 16.52% N; found: 38.70% C, 6.91% H, 16.18N.

3-Carboxypropionylalanyl-alanyl Alanine Ethylamide 300 mg. of succinic anhydride was added to a solution comprising 260 mg. of alanyl-alanyl alanine ethylamide in 5 ml. of dimethylformamide and 30 ml. of tetrahydrofuran. The reaction solution was heated for 2 hours under a reflux condenser. Then, a crystalline product separated and was filtered off, washed with tetrahydrofuran and ether. 180 mg. of a product having a melting point of 285 to 287 degrees C. was obtained by crystallization from water (13 ml.).

For $C_{15}H_{26}N_4O_6$ (359.2) $[\alpha]_D^{20} -61.8°$ (c 0.3; methyl alcohol): calculated: 50.16% C, 7.30% H, 15.60% N; found: 50.10% C, 7.40% H, 15.61% N.

4-Carboxybutyrylalanyl-alanyl Alanine Ethylamide

This compound was prepared by a process analogous to that employed for the 3-carboxypropionyl derivative by acylation with glutaric anhydride in a 65% yield and having a melting point of 278 to 280 degrees C.

$[\alpha]_D^{20} -86.0°$ (c 0.3; 50% methyl alcohol).

For $C_{16}H_{28}N_4O_5$ (372.4): calculated: 51.60% C, 7.58% H, 15.04% N; found: 51.24% C, 7.68% H, 14.90% N.

EXAMPLE 2

Benzyloxycarbonyl Alanine Phenylethylamide

This compound was prepared by a process analogous to that employed for the corresponding ethylamide described in EXample 1 in a yield of 87% and having a melting point of 125 to 126 degrees C.

For $CC_{19}H_{22}N_2O_3$ (326.3): $[\alpha]_D^{20} -2.7°$ (c 0.3; diemthylformamide): calculated: 69.94% C, 6.80% H, 8.59% N; found: 70.32% C, 7.01% H, 8.70% N.

Benzyloxycarbonylalanyl Alanine Phenylethylamide 5.5 grams of N, N-dicyclohexyl carbodiimide was added to 4.9 grams of the solution of alanine phenylethylamide liberated from the corresponding benzyloxycarbonyl derivative released by 36% hydrogen bromide in acetic acid ($R_f 0.44/S_1$; $0.58/S_2$) and 5.6 grams of benzyloxycarbonyl alanine in 200 ml. of dimethylformamide cooled to $-5$ degrees C. After 1 hour of stirring at 0 degrees of C. and 3 hours at room temperature, the separated N, N-dicyclohexylurea was filtered off, washed with dimethylformamide and the filtrate evaporated under vacuum. A crystalline evaporation residue was rubbed gradually with 1M hydrochloric acid, water, a 5% solution of sodium hydrogen carbonate, water, and crystallized from a mixture of 150 ml. of ethyl alcohol and 100 ml. of water. 7.75 g of a product having a melting point of 211 to 212 degrees C. was obtained.

$[\alpha]_D^{20} -1.95°$; (c 0.3; dimethylformamide).

For $C_{22}H_{27}N_3O_4$ (3.97.5): calculated: 66.55% C, 6.85% H, 10.57% N; found: 66.89% C, 6.99% H, 10.74% N.

Alanyl Alanine Phenylethylamide

This compound was prepared by a process analogous to that employed for alanyl-alanyl alanine ethylamide in Example 1 in a 93% yield having a melting point of 107 to 110 degrees C. $R_f 0.31/S_1$; $0.63/S_2$.

$[\alpha]_D^{20} -0.44.9°$ (c 0.3; methyl alcohol).

For $C_{14}H_{21}N_3O_2$ (263.4): calculated: 63.85% C, 8.04% H, 15.96% N; found: 63.38% C, 8.14% H, 16.20% N.

3-Carboxypropionylalanyl Alanine Phenylethylamide

This compound was prepared by a process analogous to that employed for 3-carboxypropionylalanyl-alanyl alanine ethylamide in Example 1 in a 63% yield having a melting point of 209 to 211 degrees C.

$[\alpha]_D^{20} -45.3°$ (c 0.3; 50% methyl alcohol).

For $C_{18}H_{25}N_3O_5$ (364.2): calculated: 59.37% C, 6.92% H, 11.54% N; found: 59.22% C, 6.85% H, 11.82% N.

4-Carboxybutyrylalanyl Alanine Phenylethylamide

This compound was prepared by a process analogous to that employed for 4-carboxybutyrylalanyl-alanyl alanine ethylamide in Example 1 in a 57% yield having a melting point of 208 to 209 degrees C.

$[\alpha]_D^{20} -61.4°$ (c 0.3; methyl alcohol).

For $C_{19}H_{27}N_3O_4$ (377.5): calculated: 60.46% C, 7.21% H, 11.13% N; found: 59.58% C, 7.19% H, 11.25% N.

EXAMPLE 3

Proline Ethylamide 40 ml. of 36% hydrogen bromide in acetic acid was added to 11 grams of a solution of benzyloxycarbonyl proline ethylamide in 10 ml. of acetic acid. After 1 hour 300 ml. of ether was added to the reaction solution, so resulting in the separation of a non-crystalline hydrobromide. The hydrobromide was dried for 2 hours in desiccator over phosphorus pentoxide and sodium hydroxide, and then suspended in 60 ml. of a saturated amoniacal solution of chloroform at 0 degrees C. The resultant suspension was permitted to stand at 3 degrees C. for 20 minutes and then filtered, the filtrate being evaporated. 5.7 g of a non-crystalline product was obtained. $R_f 0.25/S_1$; $0.56/S_2$.

Benzyloxycarbonylalanyl Proline Ethylamide 9.0 grams of N, N-dicyclohexylcarbodiimide was added to a solution of 5.6 grams of proline ethylamide and 9.0 grams of benzyloxycarbonyl alanine in a mixture of 5 ml. of dimethylformamide and 60 ml. of tetrahydrofuran cooled to $-5$ degrees C. After 1 hour of stirring at 0 degrees C., the reaction mixture was permitted to stand for 12 hours at room temperature, so resulting in the separation of N, N-dicyclohexylurea which was filtered off. The filtrate was evaporated; the evaporation residue dissolved in a mixture of ethyl acetate and water. The organic phase formed was gradually shook with 1M hydrochloric acid, water, 5% sodium hydrogen carbonate, with water, dried with anhydrous sodium sulphate and evaporated. The evaporation residue was crystallized from a mixture of 30 ml. of ether and 30 ml. of petroleum ether. 5.4 g of a product having a melting point of 99 to 101 degrees C. was obtained.

$[\alpha]_D^{20} -93.4°$ (c 0.3; methyl alcohol).

For $C_{18}H_{25}N_3O_4$ (347.4): calculated: 62.23% C, 7.25% H, 12.09% N; found: 62.13% C, 7.44% H, 11.70% N.

Alanyl Proline Ethylamide

This compound was prepared by a process analogous to that employed for proline ethylamide in quantitative yield from the corresponding benzyloxycarbonyl derivative. $R_f 0.13/S_1$; $0.57/S_2$.

3-Carboxypropionylalanyl Proline Ethylamide 500 mg of succinic anhydride was added to a solution of 500 mg of alanyl proline ethylamide in form of dioxane (10 ml) and 0.25 ml of dimethylformamide and the reaction solution heated under reflux for 30 minutes. Then the solution was evaporated and the residue crystallized from 10 ml of acetone and 30 ml of ether. 510 mg of a product having a melting point of 139 to 141 degrees C. was obtained. $[\alpha]_D^{20} -129.2$ degrees (c 0.3; 50% methyl alcohol).

For $C_{15}H_{26}N_4O_6$ (359.2): calculated: 53.53% C, 7.38% H, 13.38% N; found: 52.90% C, 7.45% H, 12.98% N.

EXAMPLE 4

Benzyloxycarbonylalanyl-ananyl Proline Ethylamide 1.6 g of N,N-dicyclohexylcarbodiimide was added to a solution of alanyl proline ethylamide prepared from 2.45 g of a benzyloxycarbonyl derivative by the reaction of 36% hydrogen bromide in acetic acid followed by liberation at Merolit FF in OH-cycle in 20 ml of dimethylformamide and 1.55 grams of benzyloxycarbonyl alanine cooled to −5 degrees C. After 1 hour of stirring at 0 degree C and 12 hours standing at 3 degrees C., N,N-dicyclohexylurea separated and was filtered off, the filtrate being evaporated. A non-crystalline evaporation residue was then dissolved in 50 ml of ethyl acetate and after 12 hours standing at 3 degrees C. the separated product was filtered off. 1.75 g of a product having a melting point of 138 to 139 degrees C. was obtained. $[\alpha]_D^{20} -47.0$ degrees (c 0.3; dimethylformamide).

For $C_{21}H_{30}N_4O_5$ (418.5): calculated: 60.27% C, 7.23% H, 13.39% N; found: 59.97% C, 7.21% H, 13.12% N.

Benzyloxycarbonylalanyl-alanyl Proline Ethylamide 11 grams of N,N-dicyclohexylcarbodiimide was added to a solution of 14.7 grams of benzyloxycarbonylalanyl alanine in 100 ml of dimethylformamide and 7.6 g of proline ethylamine (prepared from the corresponding benzyloxycarbonyl derivative) cooled to −5 degrees C. and the reaction mixture treated by conventional techniques. 10.6 g of product having a melting point of 139 to 140 degrees C. was obtained. $[\alpha]_D^{20} -46.5$ degrees (c 0.3; dimethylformamide).

For $C_{21}H_{30}N_4O_5$ (418.5): calculated: 60.27% C, 7.23% H, 13.39% N; found: 60.08% C, 7.55% H, 13.32% N.

Alanyl-alanyl Proline Ethylamide

This compound was prepared from the corresponding benzyloxycarbonyl derivative by the procedure employed in Example 1 for the preparation of alanyl-alanyl alamine ethylamide. The product ws obtained in a 69% yield with a melting point of 109 to 111 degrees C. $R_f 0.14/S_1$; $0.42/S_2$.

$[\alpha]_D^{20} -126.1$ degrees (c 0.3; methyl alcohol).

For $C_{13}H_{24}N_4O_3$ (284.4) calculated: 54.91% C, 8.51% C, 8.51% H, 19.70% N; found: 54.43% C, 8.61% H, 19.44% N.

4-Carboxybutyrylalanyl-alanyl Proline Ethylamide 1.7 g of glutaric anhydride was added to a solution of 4.0 grams of alanyl-alanyl proline ethylamide in 25 ml of dimethylformamide and the reaction solution heated for 1 hour at 60 degrees C. Then, the solution was evaporated and the resultant non-crystalline evaporation residue dissolved in 30 ml of ethyl acetate. After 48 hours of standing at 3 degrees C., 3.6 g of separated product was filtered off with a melting point of 154 to 156 degrees C. ($[\alpha]_D^{20} -137.3$ degrees (c 0.3; 50% methyl alcohol).

For $C_{18}H_{30}N_4O_4$ (398.5): calculated: 54.26% C, 7.59% H, 14.06% N; found: 53.96% C, 7.75% H, 13.87% N.

3-Carboxypropionylalanyl-alanyl Proline Ethylamide

This compound was prepared in the same manner described for 3-carboxypropionylalanyl-alanyl alanine ethylamide in a yield of 71% and it exhibited a melting point of 185 to 186 degrees C. $[\alpha]_D^{20} -69.3$ degrees (c 0.3; dimethylformamide).

For $C_{17}H_{28}N_4O_6$ (385.2): calculated: 53.01% C, 7.33% H, 14.55% N; found: 52.75% C, 7.45% H, 14.44% N.

EXAMPLE 5

Benzyloxycarbonyl Alanine Isobutylamide 14 ml of chloro-sec. butyl formate added at −10 degrees C. to a solution of 23 grams of benzyloxycarbonyl alanine in 200 ml of methylene chloride and 14 ml of N-ethyl piperidine, 20.7 g of a product having a melting point of 109 to 111 degrees C. was obtained by the procedure described in Example 1 by crystallization from 60 ml of ethyl acetate and 200 ml of petroleum ether $[\alpha]_D^{20}$ 8.7 degrees (c 0.3; dimethylformamide).

For $C_{15}H_{22}N_2O_3$ (278.4): calculated: 64.73% C, 7.97% H, 10.06% N; found: 64.45% C, 8.01% H, 9.83% N.

Alanine Isobutylamide

This compound was prepared from the corresponding benzyloxycarbonyl derivative by a process analogous to that described in Example 1.

$R_f 0.32$ ($S_1$; $0.69)S_2$.

Benzyloxycarbonylalanyl-alanyl Alanine Isobutylamide

This compound was prepared by a process analogous to that employed for the corresponding benzyloxycarbonylalanyl-alanyl alanine ethylamide in a 58% yield having a melting point of 260 to 262 degrees C. $[\alpha]_D^{20} -10.9$ degrees (c 0.3; dimethylformamide).

For $C_{12}H_{32}N_4O_5$ (420.5): calculated: 59.98% C, 7.67% H, 13.32% N; found: 59.63% C, 7.70% H, 13.20% N.

Alanyl-alanyl Alanine Isobutylamide

This compound was prepared by a process analogous to that employed from the corresponding alanyl-alanyl alanine ethylamide in a 76% yield with a melting point of 249 to 252 degrees C. $R_f 0.28(S_1; 0.68)S_2$.

$[\alpha]_D^{20} -66.4$ degrees (c 0.3; methyl alcohol).

For $C_{13}H_{26}N_4O_3 \cdot H_2O$ (304.4) calculated: 51.30% C, 9.27% H, 18.41% N; found: 51.10% C, 8.73% H, 18.71% N.

An analytical sample of alanyl-alanyl alanine isobutylamide hydrobromide was crystallized from methyl alcohol and ether, having a melting point of 214 to 216 degrees C.

For $C_{13}H_{26}N_4O_3 \cdot HBr$ (367.3) calculated: 42.51% C, 7.41% H, 15.25% N; found: 42.54% C, 7.36% H, 15.23% N.

3-Carboxypropionylalanyl-alanyl Alanine Isobutylamide

This compound was prepared by a process analogous to that employed for the corresponding ethylamide derivative in an 81% yield with a melting point of 283 to 286 degrees C. $[\alpha]_D^{20} -58.2$ degrees (c 0.3; dimethylformamide).

For $C_{17}H_{30}N_4O_6$ (387.2): calculated: 52.74% C, 7.81% H, 14.47% N; found: 52.34% C, 7.93% H, 14.58% N.

4-Carboxybutyrylalanyl-alanyl Alanine Isobutylamide

This compound was prepared by a process analogous to that employed for the ethylamide derivative described in Example 1 in a 69% yield with a melting point of 292 to 293 degrees C. $[\alpha]_D^{20} -82.7$ degrees (c 0.3; 50% methyl alcohol).

For $C_{18}H_{32}N_4O_5$ (400.5): calculated: 53.99% C, 8.05% H, 13.99% N; found: 54.33% C, 7.88% H, 14.19% N.

EXAMPLE 6

Benzyloxycarbonyl Alanine Propylamide

This compound was prepared by a process analogous to that employed in the preparation of carbonyl alanine ethylamide in Example 1 in an 87% yield with a melting point of 118 to 119 degrees C. $[\alpha]_D^{20}$ 8.4 degrees (c 0.3; dimethylformamide).

For $C_{14}H_{20}N_2O_3$ (264.3) calculated: 63.62% C, 7.63% H, 10.60% N; found: 63.64% C, 7.74% H, 10.46% N.

Benzyloxycarbonylalanyl-alanyl Alanine Propylamide

This compound was prepared by a process analogous to that employed in preparing the corresponding ethylamide described in Example 1 in a 56% yield with a melting point of 268 to 269 degrees C. $[\alpha]_D^{20} -10.6$ degrees (c 0.3; dimethylformamide).

For $C_{20}H_{30}N_4O_5$ (406.5): calculated: 59.10% C, 7.44% H, 13.78% N; found: 58.74% C, 7.61% H, 123.78% N.

Alanyl-alanyl Alanine Propylamide

This compound was prepared by a process analogous to that employed in preparing alanyl-alanyl alanine ethylamide described in Example 1 in a 71% yield with a melting point of 265 to 268 degrees C. $R_f$ 0.18/$S_1$; 0.57/$S_2$.

$[\alpha]_D^{20} -82.1$ degrees (c 0.3; 50% methyl alcohol).

For $C_{12}H_{24}N_4O_3$ (272.4): calculated: 52.92% C, 8.88% H, 20.57% N; found: 53.15% C, 8.87% H, 20.54% N.

3-Carboxypropionylalanyl-alanyl Alanine Propylamide

This compound was prepared by a process analogous to that employed in preparing the corresponding ethylamide derivative described in Example 1 in an 88% yield and a melting point of 284 to 287 degrees C.

$[\alpha]_D^{20} -59.1$ degrees (c 0.3; 50% methyl alcohol).

For $C_{16}H_{28}N_4O_6$ (373.2): calculated: 51.50% C, 7.56% H, 15.01% N; found: 51.69% C, 7.52% H, 14.67% N.

4-Carboxybutyrylalanyl-alanyl Alanine Propylamide

This compound was prepared by a process analogous to that employed in preparing the corresponding ethylamide derivative described in Example 1 in an 89% yield with a melting point of 283 to 285 degrees C.

$[\alpha]_D^{20} -84.7$ degrees (c 0.3; 50% methyl alcohol).

For $C_{17}H_{30}N_4O_5$ (386.5): calculated: 52.84% C, 7.82% H, 14.50% N; found: 53.24% C, 7.92% H, 14.55% N.

EXAMPLE 7

Benzyloxycarbonyl Proline Propylamide

This compound was prepared by a process analogous to that employed in preparing the corresponding ethylamine derivative of benzyloxycarbonyl alanine described in Example 1 in an 83% yield with a melting point of 74 to 75 degrees C.

For $C_{16}H_{22}N_2O_3$ (290.4): calculated: 66.19% C, 7.64% H, 9.65% N; found: 66.05% C, 7.41% H, 9.52% N.

Proline Propylamide

This compound was prepared by a process analogous to that employed in preparing proline ethylamide in Example 3. $R_f$ 0.21($S_1$; 0.62)$S_2$.

Benzyloxycarbonylalanyl Proline Propylamide

This compound was prepared by a process analogous to that employed in preparing the corresponding ethylamide described in Example 3 in a 73% yield with a melting point of 117 to 120 degrees C.

For $C_{19}H_{27}N_3O_4$ (361.4): calculated: 63.14% C, 7.53% H, 11.63% N; found: 63.03% C, 7.39% H, 11.28% N.

Alanyl Proline Propylamide

This compound was prepared by a process analogous to that employed in preparing the corresponding ethylamide described in Examples 1 and 3 and a 79% yield. $R_f$ 0.14 ($S_1$; 0.49)$S_2$.

Benzyloxycarbonylalanyl-alanyl Proline Propylamide

This compound was prepared by a process analogous to that employed in preparing benzyloxycarbonyl alanine ethylamide from benzyloxycarbonyl alanine and alanyl proline propylamide in a 71% yield with a melting point of 101 to 103 degrees C. $[\alpha]_D^{20} -47.7$ degrees (c 0.3; dimethylformamide).

For $C_{22}H_{32}N_4O_5$ (432.5): calculated: 61.09% C, 7.46% H, 12.95% N; found: 61.11% C, 7.69% H, 12.98% N.

Alanyl-alanyl Proline Propylamide

This compound was prepared by a process analogous to that employed in preparing the corresponding ethylamide described in Example 4 in a 68% yield with a melting point of 103 to 105 degrees C. $R_f$ 0.12($S_1$; 0.56)$S_2$.

$[\alpha]_D^{20} -135.3$ degrees (c 0.3; methyl alcohol).

For $C_{14}H_{26}N_4O_3$ (298.4): calculated: 56.35% C, 8.78% H, 18.78% N; found: 55.87% C, 8.93% H, 18.78% N.

4-Carboxybutyrylalanyl-alanyl Proline Propylamide

This compound was prepared by a process analogous to that employed in preparing the corresponding ethylamide described in Example 4 in a 73% yield with a melting point of 131 to 134 degrees C. $[\alpha]_D^{20} = 148.7$ degrees (c 0.3; 50% methyl alcohol).

For $C_{19}H_{32}N_4O_4$ (412.5): calculated: 55.32% C, 7.82% H, 13.58% N; found: 55.25% C, 7.99% H, 13.74% N.

EXAMPLE 8

Benzyloxycarbonylprolyl Alanine Methyl Ester 11.0 grams of N,N-dicyclohexylbodiimide was added to a solution of 12.45 grams of benzyloxycarbonyl proline and alanine methyl ester released from 7.0 grams of the corresponding hydrochloride using 7 ml of N-ethyl piperidine in 40 ml of methylene chloride cooled to $-5$ degrees C. The resultant reaction suspension was stirred for 1 hour at 0 degree C. N,N-dicyclohexylurea separated from the suspension and was filtered off after it was allowed to stand for 12 hours at 3 degrees C. Then, the filtrate was successively washed with 1M hydrochloric acid, water, 5% sodium hydrogen carbonate, with water, dried with anhydrous sodium sulfate and evaporated. A solid evaporation residue was crystallized from 100 ml of ethyl acetate and 500 ml of petroleum ether. 12.2 g of a product having a melting point of 45 to 49 degrees C. was obtained.

Benzylcarbonylprolyl Alanine Hydrazide 7.5 ml of 80% hydrazine-hydrate was added to a solution of 10.0 grams of benzyloxycarbonylprolyl alanine methyl ester in 100 ml of methyl alcohol and the reaction solution heated under reflux for 2 hours. The solution was then evaporated and a solid evaporation residue was crystallized from 40 ml of water. 6.8 g of a product having a melting point of 142 to 143 degrees C. was obtained.

For $C_{16}H_{22}N_4O_4$ (334.4): calculated: 57.47% C, 6.63% H, 16.76% N; found: 57.41% C, 6.85% H, 16.90% N.

Benzyloxycarbonylprolyl-alanyl Alanine Ethylamide

This product was prepared by a process analogous to that employed in preparing the corresponding benzyloxycarbonylalanylalanyl alanine ethylamide described in Example 1 from benzyloxycarbonylprolyl alanine hydrazide and alanine ethylamide in a 49% yield with a melting point of 219 to 220 degrees C. $[\alpha]_D^{20} - 36.2$ degrees (c 0.3; dimethylformamide).

For $C_{21}H_{30}N_4O_5$ (418.5): calculated: 60.27% C, 7.23% H, 13.39% N; found: 60.08% C, 7.41% H, 13.22% N.

Propyl-alanyl Alanine Ethylamide

This compound was prepared by a process analogous to that employed in preparing alanyl-alanyl alanine ethylamide described in Example 1 in a 53% yield with a melting point 216 to 219 degrees C. $R_f$: 0.07($S_1$; 0.54)$S_2$.

For $C_{13}H_{24}N_4O_3$ (284.4): calculated: 54.91% C, 8.51% H, 19.17% N; found: 54.49% C, 8.42% H, 19.39% N.

4-Carboxybutyrylprolyl-alanyl Alanine Ethylamide

This compound was prepared by a process analogous to that employed in preparing 4-carboxybutyryl-alanyl-alanyl alanine ethylamide described in Example 1 in a 44% yield with a melting point of 172 to 177 degrees C.

For $C_{18}H_{30}N_4O_4$ (398.5): calculated: 54.26% C, 7.59% H, 14.06% N, found: 54.81% C, 7.43% H, 14.38% N.

EXAMPLE 9

3-Carboxyacryolylalanyl-alanyl Alanine Ethylamide 200 mg of maleic anhydride was added to a solution of 260 mg of alanyl-alanyl ethylamide in 20 ml of dimethylformamide heated to 60 degrees C. and the reaction solution heated for 30 minutes at 80 degrees C. Then, the reaction mixture was evaporated and the evaporation residue crystallized from dimethylformamide and 2-propyl alcohol. 185 mg of a product having a melting point of 260 to 266 degrees C. (decomposition) was obtained. $[\alpha]_D^{20} - 35.6$ degrees (c 0.3; dimethylformamide).

For $C_{15}H_{24}N_4O_6$ (356.4): calculated: 50.55% C, 6.79% H, 15.72% N; found: 49.97% C, 7.13% H, 15.83% N.

We claim:

1. Alkylamide of carboxyalkanoykl peptide of the formula

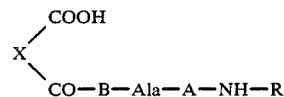

wherein
   (a) R is selected from the group consisting of straight and branched chain alkyl groups of 1–5 carbon atoms, and a lower aralkyl group,
   (b) A is a residue selected from the group consisting of peptidically bound proline and peptidically bound alanine,
   (c) B is selected from the group consisting of a peptide bond, a peptidically bound proline residue and a peptidically bound alanine residue, and
   (d) X is selected from the group consisting of $(CH_2)_n$ and $CH=CH$ groups wherein n is an integer of 1–3.

2. Alkylamide in accordance with claim 1, wherein R is phenylethyl.

* * * * *